United States Patent [19]

Austel et al.

[11] Patent Number: 4,766,130
[45] Date of Patent: Aug. 23, 1988

[54] 2-PHENYL-IMIDAZOPYRIDIN-ONES AND ALSO USEFUL AS CARDIOTONICS AND ANTI-HYPERTENSIVES

[75] Inventors: Volkhard Austel, Biberach; Joachim Heider, Warthausen; Norbert Hauel, Biberach; Manfred Reiffen, Biberach; Jacobus C. A. van Meel, Biberach; Willi Diederen, Biberach, all of Fed. Rep. of Germany

[73] Assignee: Celamerck GmbH & Co. KG, Ingelheim am Rhein, Fed. Rep. of Germany

[21] Appl. No.: 7,530

[22] Filed: Jan. 28, 1987

Related U.S. Application Data

[62] Division of Ser. No. 623,718, Jun. 22, 1984, Pat. No. 4,670,438.

[30] Foreign Application Priority Data

Jul. 5, 1983 [DE] Fed. Rep. of Germany ....... 3324115

[51] Int. Cl.⁴ .................. A61K 31/435; C07D 471/04
[52] U.S. Cl. .................................... 514/303; 546/118
[58] Field of Search ........................ 546/118; 514/303

[56] References Cited

U.S. PATENT DOCUMENTS 3,985,891 10/1976 Kutter et al. ................... 546/118
4,616,090 10/1986 Jonas .............................. 546/118

FOREIGN PATENT DOCUMENTS 0079083  5/1983 European Pat. Off. .
0093593 11/1983 European Pat. Off. .
2091249  7/1982 United Kingdom .

*Primary Examiner*—Richard A. Schwartz
*Assistant Examiner*—Bernard I. Dentz
*Attorney, Agent, or Firm*—Weissenberger, Hammond & Littell

[57]  ABSTRACT

Compounds of the formula

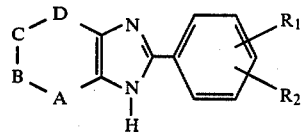

wherein
A, B, C and D are $-N=$, $HN=$, $R_3N=$, $O=C=$, $HC\equiv$, $HO-C\equiv$ or $R_3SO_2-O-C\equiv$; and
$R_1$ and $R_2$ are substituents of various types.

The compounds are useful as hypotensives and cardiotonics.

11 Claims, No Drawings

2-PHENYL-IMIDAZOPYRIDIN-ONES AND ALSO USEFUL AS CARDIOTONICS AND ANTI-HYPERTENSIVES

This is a division of copending application Ser. No. 623,718, filed June 22, 1984, now U.S. Pat. No. 4,670,438.

This invention relates to novel 2-phenyl-imidazoles and acid addition salts thereof, to methods of preparing these compounds, to pharmaceutical compositions containing them as active ingredients, and to a method of using them an antihypertensives and cardiotonics.

THE PRIOR ART

Imidazo[4,5-c]pyridines having useful pharmacological properties are disclosed in European applications No. 0,072,926 and No. 0,079,083.

THE INVENTION

More particularly, the present invention relates to a novel class of compounds represented by the formula

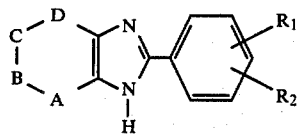

wherein
A, B, C and D are each independently

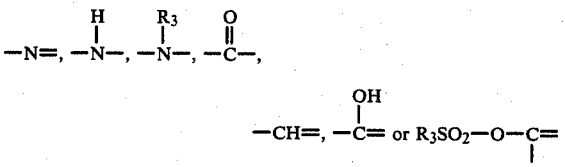

provided, however, that at least one of A, B, C and D must be HN= and another must be O=C=; or at least one of A, B, C and D must be —N= and another must be

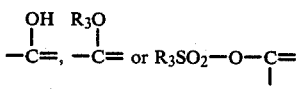

or one of A, B, C and D may also be a chlormethine group if at least two of A, B, C and D are —N=;
$R_1$ is NC—CH$_2$—O—, HOOC—CH$_2$—O—; $R_3$—OOC—CH$_2$—O—, $R_3$SO$_2$—O—, $R_3$SO$_2$—NH—, $R_3$SO$_2$—NR$_3$—, $R_4$—O—, or, when A, B, C and D together with the condensed imidazole ring is other than imidazo[4,5-c]pyridine, also hydroxyl;
$R_2$ is $R_3$O—,

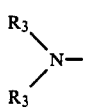

or $R_5$—O—;
$R_3$ is alkyl of 1 to 4 carbon atoms;
$R_4$ is alkynyl of 2 to 5 carbon atoms or, when A, B, C and D together with the condensed imidazole ring is other than imidazo[4,5-c]pyridine, also alkenyl of 2 to 5 carbon atoms; and
$R_5$ is alkenyl of 2 to 5 carbon atoms or alkinyl of 2 to 5 carbon atoms;

tautomers thereof; and non-toxic, pharmacologically acceptable acid addition salts thereof.

The present invention thus relates to novel imidazo[4,5-b]pyridin-5-ones, imidazo[4,5-b]pyridin-7-ones, 6-hydroxy-imidazo[4,5-b]pyridines, imidazo[4,5-c]pyridin-6-ones, imidazo[4,5-c]pyridin-4-ones, 7-hydroxy-imidazo[4,5-c]pyridines, imidazo[4,5-c]pyridazin-3-ones, imidazo[4,5-d]pyridazin-4-ones, imidazo[4,5-b]pyrazin-5-ones, purin-2-ones, purin-6-ones, purin-2,6-diones, imidazo[4,5-e]triazin-6-ones, imidazo[4,5-d]triazin-7-ones alkanesulfonyloxy-imidazo[4,5-b]pyridines, alkanesulfonyloxy-imidazo[4,5-c]pyridines, alkanesulfonyloxy-purines, alkanesulfonyloxy-imidazo[4,5-c]pyridazines, alkanesulfonyloxyimidazo[4,5-d]pyridazines, alkanesulfonyloxy-imidazo[4,5-b]pyrazines, alkoxy-imidazo[4,5-b]pyridines, alkoxy-imidazo[4,5'-c]pyridines, alkoxypurines, alkoxy-imidazo[4,5-c]pyridazines, alkoxy-imidazo[4,5-b]pyrazines, chloro-purines, chloro-imidazo[4,5-c]pyridazines, chloro-imidazo[4,5-d]pyridazines and chloroimidazo[4,5-b]pyrazines of the formula I above, tautomers and acid addition salts thereof, particularly non-toxic, pharmacologically acceptable acid addition salts thereof formed with inorganic or organic acids, processes for preparing these compounds, and pharmaceutical compositions containing them.

Examples of specific embodiments of radicals $R_1$, $R_2$ and $R_3$ the following:

$R_1$: cyanomethoxy, hydroxycarbonylmethoxy, methoxycarbonylmethoxy, ethoxycarbonylmethoxy, propoxycarbonylmethoxy, isopropoxycarbonylmethoxy, methanesulfonyloxy, ethanesulfonyloxy, propanesulfonyloxy, isopropanesulfonyloxy, n-butanesulfonyloxy, methanesulfonylamino, ethanesulfonylamino, n-propanesulfonylamino, N-methyl-methanesulfonylamino, N-isopropyl-methanesulfonylamino, N-ethyl-ethanesulfonylamino, N-n-propyl-ethanesulfonylamino, N-methyl-propanesulfonylamino, N-ethyl-propanesulfonylamino, vinyloxy, allyloxy, crotyloxy, pent-2-enyloxy, pent-3-enyloxy or propargyloxy;

$R_2$: methoxy, ethoxy, propoxy, isopropoxy, dimethylamino, diethylamino, dipropylamino, diisopropylamino, ethyl-methylamino, ethyl-propylamino, vinyloxy, allyloxy, crotyloxy, pent-2-enyloxy, pent-3-enyloxy or propargyloxy;

$R_3$: methyl, ethyl, n-propyl, isopropyl or n-butyl.

A preferred subgenus is constituted by those compounds of the formula I where
A, B, C, D, $R_1$ and $R_2$ have the meanings previously defined,
$R_3$ is methyl, and
$R_4$ and $R_5$ are each independently allyl or propargyl, especially those where $R_1$ is in the 4-position and $R_2$ is in the 2-position of the phenyl ring, and acid addition salts thereof, particularly non-toxic, pharmacologically acceptable acid addition salts thereof.

A particularly preferred subgenus is constituted by imidazo[4,5-b]pyridin-5-ones, imidazo[4,5-c]pyridin-4-ones, imidazo[4,5-c]pyridin-6-ones, imidazo[4,5-c]pyridazin-3-ones, imidazo[4,5-d]pyridazin-4-ones, imidazo[4,5-b]pyrazin-5-ones, purin-2-ones, purin-6-ones, purine-2,6-diones and imidazo-[4,5-e]triazin-6-ones of the formula I, where $R_1$ is propargyloxy, methanesulfonyloxy, methanesulfonylamino or N-methyl-methanesulfonylamino or, when A, B, C and D together with the condensed imidazole ring is other than imidazo[4,5-c]pyridine, also allyloxy; and $R_2$ is methoxy or dimethylamino, especially those where $R_1$ is in the 4-position and $R_2$ is in the 2-position of the phenyl ring, and acid addition salts thereof, particularly non-toxic, pharmacologically acceptable acid addition salts thereof.

The compounds embraced by formula I may be prepared by the following methods:

Method A

By cyclizing a compound of the formula

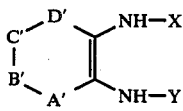
(II)

wherein

A', B', C' and D' have the meanings previously defined for A, B, C and D or one of them is an oxymethine group protected by a protective group, one of X and Y is hydrogen and the other or both X and Y are

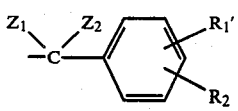

where $R_2$ has the meanings previously defined, $R_1'$ has the meanings previously defined for R, or is hydroxyl protected by a protective group;

$Z_1$ and $Z_2$ are each individually amino, substituted amino, hydroxyl, lower alkoxy, mercapto or lower alkylthio, or $Z_1$ and $Z_2$ together are oxygen, sulfur, imino, (alkyl of 1 to 3 carbon atoms)imino, (alkylene of 2 to 3 carbon atoms)dioxy or (alkylene of 2 to 3 carbon atoms)dithio;

and, if desired, subsequently splitting off residual protective groups.

The protective groups may be conventional protective groups for hydroxyl, that is, acyl such as acetyl, propionyl or benzoyl, or benzyl.

The cyclization is advantageously carried out in a solvent such as water, ethanol, isopropanol, glacial acetic acid, benzene, chlorobenzene, toluene, xylene, glycol, glycol monomethyl ether, diethyleneglycol dimethyl ether, sulfolane, dimethylformamide, tetralin or a mixture of any two of these, or in an excess of the acylating agent used to prepare the compound of the formula II, for instance in the corresponding nitrile, anhydride, acid halide, ester, amide or methiodide, for example at temperatures between 0° and 250° C., but preferably at the boiling point of the reaction mixture, optionally in the presence of a condensation agent such as phosphorus oxychloride, thionyl chloride, sulfuryl chloride, sulfuric acid, p-toluenesulfonic acid, hydrochloric acid, phosphoric acid, polyphosphoric acid, acetic acid anhydride or possibly also in the presence of a base such as sodium hydroxide, potassium ethoxide or potassium tert. butoxide. However, the cyclization may also be carried out without a solvent and/or condensing agent.

Any protective group used in the reaction is subsequently split off by hydrolysis or hydrogenation. However, if an acyl group is used as the protective group, the protective group may be split off during the reaction.

The removal of a protective group by hydrolysis is advantageously carried out in an aqueous or alcoholic solvent such as water, water/methanol, water/dioxane or methanol in the presence of an acid such as hydrochloric acid or a base such as sodium hydroxide solution or ammonia at temperatures up to the boiling point of the solvent which is used.

The removal of a protective group by hydrogenation is carried out in a solvent such as ethyl acetate, glacial acetic acid or methanol, with hydrogen in the presence of a hydrogenation catalyst such as platinum or palladium-on-charcoal, optionally in the presence of a base such as sodium hydroxide or potassium hydroxide.

Method B

By rearrangement of an N-oxide of the formula

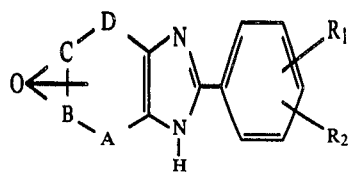
(III)

wherein A, B, C, D, $R_1$ and $R_2$ have the meanings previously defined, optionally followed by hydrolysis.

The reaction is advantageously carried out in a solvent such as benzene, in the presence of an acylating agent such as acetic acid anhydride or propionic acid anhydride which may also be used as the solvent, at elevated temperatures, but preferably at the boiling point of the solvent which is used.

The subsequent hydrolysis is advantageously carried out in water, water/methanol, water, dioxane or methanol, in the presence of an acid such as hydrochloric acid or a base such as sodium hydroxide or ammonia, at the boiling point of the reaction mixture.

Method C

For the preparation of a compound of the formula I wherein $R_1$ is alkanesulfonyloxy, alkanesulfonylamino or N-alkyl-alkanesulfonylamino and/or one of A, B, C and D is

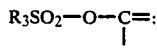

By reacting a compound of the formula

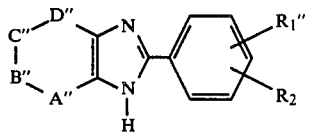
(IV)

wherein $R_2$ has the meanings previously defined, and

A", B", C", D" and $R_1$" have the meanings previously defined for A, B, C, D and $R_1$, respectively, but either $R_1''$ must be hydroxyl, amino or alkylamino or one of A", B", C" and D" must be HO—C≡,
with a sulfonyl halide of the formula $$Hal—SO_2R_3 \quad (V)$$

wherein $R_3$ has the meanings previously defined, and Hal is chlorine or bromine, followed by partial hydrolysis, if desired.

The reaction is carried out in a solvent such as water, tetrahydrofuran, dioxane or dimethylformamide, in the presence of an acid-binding agent such as sodium hydroxide, sodium hydride, potassium tert.butoxide, triethylamine, ethyl-diisopropylamine or pyridine, where the last three may also be used as solvents, at temperatures between 0° and 100° C., preferably at temperatures between 20° and 50° C.

For the preparation of a compound of the formula I wherein $R_1$ is alkanesulfonyloxy, it is advantageous to proceed via partial hydrolysis of the reaction product thus obtained.

The optional subsequent hydrolysis is advantageously carried out in water, water/methanol, water/dioxane or in an alcohol such as methanol, ethanol or isopropanol, in the presence of an acid such as hydrochloric acid, optionally by heating to the boiling point of the solvent which is used.

Method D

For the preparation of a compound of the formula I wherein $R_1$ or $R_1$ and $R_2$ is alkenyloxy or alkynyloxy or $R_2$ is alkoxy:
By reacting a compound of the formula (VI)

wherein
A, B, C and D have the meanings previously defined, and
$R_1'''$ $R_2'$ have the meanings previously defined for $R_1$ and $R_2$, respectively, but at least one of $R_1'''$ and $R_2'$ must be hydroxyl,
with a halide of the formula $$Hal—R_6 \quad (VII)$$

wherein
$R_6$ has the meanings previously defined for $R_3$, $R_4$ and $R_5$, and
Hal is chlorine, bromine or iodine.

The reaction is advantageously carried out in a solvent such as tetrahydrofuran, dioxane, dimethylformamide, sulfolane, dimethylsulfoxide or ethyleneglycol dimethyl ether, preferably in the presence of an acid binding agent such as potassium carbonate, potassium tert.butoxide or sodium hydride, at temperatures between 0° and 100° C., but preferably at temperatures between 20° and 50° C.

The compounds embraced by formula I are basic and therefore form addition salts with inorganic or organic acids. Examples of non-toxic, pharmacologically acceptable acid addition salts are those formed with hydrochloric, hydrobromic, sulfuric, phosphoric, fumaric, succinic, tartaric, citric, lactic, maleic or methanesulfonic acid.

The starting compounds of the formulas II to VII are either known from the literature or may be obtained by methods described in the literature. For example, the starting compounds of the formula II may be obtained by acylation of the corresponding o-diamino compounds or by reduction of the corresponding acylamino-nitro compounds, while the compounds of the formula IV or VI may be obtained by subsequent cyclization, and the compounds of the formula III are obtained by additional N-oxidation (see British Pat. No. 810,545 and European Application No. 024,290).

The following examples illustrate the present invention and will enable others skilled in the art to understand it more completely. It should be understood, however, that the invention is not limited solely to the particular examples given below.

EXAMPLE 1

2-(2-Methoxy-4-methanesulfonyloxy-phenyl)-4H-imidazo[4,5-b]pyridin-5-one (a)
2-(2-Methoxy-4-methanesulfonyloxy-phenyl)imidazo[4,5-b]pyridin-4-oxide 3.19 g of 2-(2-methoxy-4-methanesulfonyloxy-phenyl)imidazo[4,5-b]pyridine were dissolved in 25 ml of and then 5 ml of 30% hydrogen peroxide were added dropwise thereto. The mixture was refluxed for one hour and concentrated to about one-tenth of its volume. The residue was poured onto ice and digested until it had crystallized throughout. Yield: 2.1 g (63% of theory). Melting point: 110°-125° C.

(b)
2-(2-Methoxy-4-methanesulfonyloxy-phenyl)-4H-imidazo[4,5-b]pyridin-5-one 2 g of the product obtained in (a) were dissolved in 20 ml of acetic acid anhydride, and the solution was refluxed for 2.5 hours. Thereafter, the solution was concentrated by evaporation in vacuo, the residue was mixed with 10 ml of 2N hydrochloric acid, and the mixture was boiled for 20 minutes while stirring. After it had cooled, the reaction product was precipitated by the addition of sodium acetate and purified by chromatography on silica gel (eluant: methylene chloride/ethanol 1:0 to 1:0.1). Yield: 0.72 g (36% of theory). Melting point: 258°-259° C. (decomp.).

The following compounds were obtained analogously:
2-(2-Methoxy-4-propanesulfonyloxy-phenyl)-4H-imidazo[4,5-b]pyridin-5-one,
Melting point: 193°-195° C.
2-(2-Methoxy-4-ethanesulfonyloxy-phenyl)-4H-imidazo[4,5-b]pyridin-5-one, Melting point: 241°-244° C.
2-(2-Methoxy-4-isopropylsulfonyloxy-phenyl)-4H-imidazo[4,5-b]pyridin-5-one, Melting point: 258°-261° C.
2-(2-Methoxy-4-n-butylsulfonyloxy-phenyl)-4H-imidazo[4,5-b]pyridin-5-one, Melting point: 203°-205° C.

EXAMPLE 2

2-(2-Methoxy-4-methanesulfonylamino-phenyl)-4H-imidazo[4,5-b]pyridin-5-one 2.7 g of 5-amino-6-(2-methoxy-4-methanesulfonylaminobenzoyl-amino)-2-pyridone were refluxed in 50 acetic acid for 1.5 hours. The mixture was then concentrated by evaporation in vacuo, and the residue was purified on silica gel (eluant: methylene chloride/ethanol 1:0 to 1:0.1). Yield: 0.1 g (4% of theory). Melting point: above 255° C.

Calculated: C-50.29%; H-4.22%; N-16.76%; S-9.54%. Found: C-49.95%; H-4.48%; N-16.52%; S-9.49%.

The following compounds were obtained analogously:

2-(2-methoxy-4-methanesulfonylamino-phenyl)-4H-imidazo[4,5-d]pyridazin-4-one, Melting point: 310°-314° C. (decomp.).

8-(2-methoxy-4-methanesulfonyloxy-phenyl)-1H,3H-purin-2,6-dione, Melting point: 305°-307° C. (decomp.).

8-(2-methoxy-4-methanesulfonylamino-phenyl)-3(1)H-purin-2-one, Melting point: 230°-232° C.

8-(2-methoxy-4-cyanomethoxy-phenyl)-3(1)H-purin-2-one, 8-(2-methoxy-4-propargyloxy-phenyl)-3(1)H-purin-2-one, Melting point: above 300° C.

Calculated: C-60.80%; H-4.08%; N-18.91%. Found: C-60.96%; H-4.09%; N-18.32%.

2-(2-methoxy-4-cyanomethyloxy-phenyl)-5H-imidazo[4,5-c]pyridin-4-one, 2-(2-methoxy-4-ethoxycarbonylmethyloxy-phenyl)-5H-imidazo[4,5-c]pyridin-4-one, 2-(2-methoxy-4-carboxymethyloxy-phenyl)-5H-imidazo[4,5-c]pyridin-4-one, 2-(2-methoxy-4-allyloxy-phenyl)-5H-imidazo[4,5-c]pyridin-4-one, 8-[2-dimethylamino-4-(N-methyl-N-methanesulfonylamino)phenyl]-3(1)H-purin-2-one, 2-(2-dimethylamino-4-methanesulfonylamino-phenyl)-4H-imidazo[4,5-b]pyridin-5-one.

EXAMPLE 3

8-(2-Methoxy-4-methanesulfonyloxy-phenyl)-3(1)H-purine-2-one 1 g of 8-(2-methoxy-4-hydroxyphenyl)-3(1)H-purin-2-one was suspended in 10 ml of pyridine. 2 ml of methanesulfonyl chloride were added dropwise while stirring. The mixture was stirred for 15 minutes more, then 3 ml of water were added, and the mixture was concentrated by evaporation in vacuo. The residue was combined with water, and the solid product which precipitated was purified on silica gel (eluant: methanol). Yield: 0.11 g (8.5% of theory). Melting point: 233°-235° C. (decomp.).

The following compounds were obtained analogously:

2-(2-methoxy-4-methanesulfonyloxy-phenyl)-4H-imidazo[4,5-d]pyridazin-4-one (in the work-up step, hydrochloric acid was added and the mixture was digested), Melting point: 294°-296° C. (decomp.).

2-(2-methoxy-4-methanesulfonyloxy-phenyl)-5(7)H-imidazo[4,5-e]triazin-6-one, 2-(2-methoxy-4-methanesulfonyloxy-phenyl)-4H-imidazo[4,5-c]pyridin-6-one (in the work-up step, hydrochloric acid was added), 8-(2-dimethylamino-4-methanesulfonyloxy-phenyl)-(1)H-purin-2-one, 2-(2-dimethylamino-4-methanesulfonyloxy-phenyl)-5H-imidazo [4,5-c]pyridin-4-one, 8-(2-dimethylamino-4-methanesulfonylamino-phenyl)-1H,3H-purin-2,6-dione, 6-methoxy-2-(2-methoxy-4-methanesulfonyloxy-phenyl)imidazo[4,5-c]pyridine, Melting point: 231° C. (decomp.).

2-(2-methoxy-4-methanesulfonylamino-phenyl)-4H-imidazo[4,5-d]pyridazin-4-one, Melting point: 310°-314° C. (decomp.).

6-(2-methoxy-4-methanesulfonyloxy-phenyl)-5H-imidazo[4,5-c]pyridazin-3-one, 6-(2-methoxy-4-methanesulfonylamino-phenyl)-5H-imidazo[4,5-c]pyridazin-3-one, Melting point: 320°-322° C. (decomp.)

2-methoxy-8-(2-ethoxy-4-methanesulfonyloxy-phenyl)-purin, Melting point: 127°-130° C.

2-methoxy-8-(2-propoxy-4-methanesulfonyloxy-phenyl)purin, Melting point: 173°-175° C.

8-(2-ethoxy-4-methanesulfonyloxy-phenyl)-3(1H)-purin-2-one, 8-(2-propoxy-4-methanesulfonyloxy-phenyl)-3(1H)-purin-2-one.

EXAMPLE 4

2-(2-Methoxy-4-methanesulfonyloxy-phenyl)-4-methanesulfonyloxy-imidazo[4,5-c]pyridine 1 g of 2-(2-methoxy-4-hydroxy-phenyl)-5H-imidazo[4,5-c]pyridin-4-one was suspended in 10 ml of pyridine. After the addition of 2 ml of methanesulfonyl chloride, the mixture was stirred for 2 hours more at room temperature. The reaction mixture was mixed with water, and the reaction product was thus precipitated. Yield: 1.08 g (77% of theory). Melting point: decomposition from 164° C.

Calculated: C-43.58%; H-3.66%; N-10.16%; S-15.51%. Found C-43.30%; H-3.75%; N-10.05%; S-15.73%.

The following compound was obtained analogously:

2-(2-methoxy-4-methanesulfonyloxy-phenyl)-6-methanesulfonyloxy-imidazo[4,5-b]pyridine, Melting point: 188°-189° C.

EXAMPLE 5

2-(2-Methoxy-4-methanesulfonyloxy-phenyl)-5H-imidazo[4,5-c]pyridin-4-one hydrochloride 0.65 g of 2-(2-methoxy-4-methanesulfonyloxy-phenyl)-4-methanesulfonyloxy-imidazo [4,5-c]pyridine was dissolved in 35 ml of ethanolic hydrochloric acid, and the solution was stirred for an hour at room temperature. The precipitate which had formed was suction-filtered off and washed with ethanol. Yield: 0.53 g (91% of theory). Melting point: 193°-195° C. (decomp.).

EXAMPLE 6

2-(2-Methoxy-4-propargyloxy-phenyl)-5H-imidazo[4,5-c]pyridin-4-one 1 g of 2-(2-methoxy-4-hydroxy-phenyl)-5H-imidazo[4,5-c]pyridin-4-one was suspended in 30 1.41 g of potassium carbonate were added, and the mixture was stirred at room temperature. After 15 minutes and again after one hour, 0.9 ml of propargyl bromide was added, and the mixture was then stirred for another 1.25 hours. The solvent was substantially evaporated in vacuo, and the residue was stirred with methylene chloride. After the precipitate had been filtered off and washed with water, the product contained in the organic phase was purified on a silica gel column (eluant: methylene chloride/ethanol 1:0 to 1:0.03). The product crystallized with half a mol of ethanol. Yield: 0.07 g (7% of theory). Melting point: 178°-180° C.

EXAMPLE 7

2-(2-Methoxy-4-methanesulfonyloxy-phenyl)-4H-imidazo[4,5-b]pyrazin-5-one

This compound was prepared analogous to Example 1(b) from 0.75 g of 2-(2-methoxy-4-methanesulfonyloxy-phenyl) imidazo[4,5-b]pyrazin-4-oxide (heated for 1.5 hours with acetic acid anhydride). Yield: 0.13 g (17% of theory). Melting point: above 260° C.

Calculated: C-46.44%; H-3.60%; N-16.66%; S-9.55%. Found: C-46.34%; H-3.86%; N-16.50%; S-9.29%.

EXAMPLE 8

2-(2-Methoxy-4-methanesulfonyloxy-phenyl)-5-methanesulfonyloxy-imidazo[4,5-b]pyridine and 2-(2-Methoxy-4-hydroxy-phenyl)-5-methanesulfonyloxyimidazo [4,5-b]pyridine 1.6 g of 2-(2-methoxy-4-hydroxy-phenyl)-4H-imidazo-[4,5-b]pyridin-5-one were dissolved in 25 ml of pyridine, the solution was mixed with 0.6 ml of methanesulfonyl chloride, and the mixture was stirred overnight at room temperature. 50 ml of ice were added, and the mixture was made acid with 20 ml of concentrated hydrochloric acid. It was then heated for 1.5 hours on a steam bath, then cooled, and the product which precipitated was purified by chromatography on silica gel (eluant: methylene chloride/ethanol 1:0.01 to 1:0.2).

Fraction I:

Yield: 0.18 g (10% of theory) of 2-(2-methoxy-4-methane sulfonyloxy-phenyl)-5-methanesulfonyloxy-imidazo[4,5-b]pyridine, Melting point: 223°-225° C.

Fraction II:

Yield: 0.21 g (15% of theory) of 2-(2-methoxy-4-hydroxyphenyl)-5-methanesulfonyloxy-imidazo[4,5-b]pyridine, Melting point: 227°-228° C.

EXAMPLE 9

2-(2-Methoxy-4-hydroxy-phenyl)-4H-imidazo[4,5-b]pyridin-5-one 3.95 g of 5-nitro-6-(2-methoxy-4-benzyloxy-benzoylamino)-2-pyridone were hydrogenated in 350 ml of glacial acetic acid after the addition of 1 g of 10% palladium-on-charcoal for 1.7 hours at 80° C. under a pressure of 5 bar. The reaction mixture was then stirred at 100° C. for 1.3 hours. The catalyst was filtered off, and the filtrate was allowed to cool. The product which precipitated was washed with ether. By evaporating the filtrate and adding ether, further fractions were obtained. Yield: 2.3 g (60% of theory). Melting point: over 270° C.

Calculated: C-54.10%; H-5.07%; N-11.13%. Found: C-54.38%; H-4.96%; N-11.04%.

EXAMPLE b 10

2-(2-Methoxy-4-methanesulfonylamino-phenyl)-6-hydroxy-imidazo[4,5-b]pyridine 0.5 g of 2,3-diamino-5-acetoxy-pyridine and 0.83 g of 2-methoxy-4-methanesulfonylamino-benzoic acid were refluxed for one hour in 20 ml of phosphorus oxychloride. The reaction mixture was combined with ice water and then adjusted to pH 7 with concentrated aqueous ammonia. The product was then extracted with ethyl acetate and purified by column chromatography (silica gel, eluant: methylene chloride/ethanol 1:0.02 to 1:0.1). Yield: 0.06 g (6% of theory). Melting point: 225° C. (decomp.).

The following compound was obtained analogously: 2-methoxy-8-(2-methoxy-4-propargyloxy-phenyl)purine. Melting point: 148°-150° C.

EXAMPLE 11

2-Chloro-8-(2-methoxy-4-propargyloxy-phenyl)purine 2.5 g of 2-chloro-8-(2-methoxy-4-propargyloxy-benzoylamino)-5-amino-pyrimidine were dissolved in a mixture of 50 ml of 2N sodium hydroxide and 50 ml of ethanol, and the solution was refluxed for 2 hours. The mixture was diluted with 50 ml of ice water, and a precipitate was obtained by acidifying with glacial acetic acid. The precipitate was suction-filtered off, taken up in acetone/methylene chloride, and the solution was dried over magnesium sulfate and evaporated to dryness in vacuo. The residue was triturated with ether and suctionfiltered. Yield: 1.4 g (64% of theory). Melting point: 229°-231° C. (decomp.).

EXAMPLE 12

8-(2-Methoxy-4-methanesulfonyloxy-phenyl)-purin-6-one (a)

6-Methanesulfonyloxy-8-(2-methoxy-4-methanesulfonyloxy-phenyl)purine

This compound was prepared analogous to Example 4. The product was used in the next step without any further purification.

(b)

8-(2-Methoxy-4-methanesulfonyloxy-phenyl)purin-6-one

This compound was prepared analogous to Example 5 from 6-methanesulfonyloxy-8-(2-methoxy-4-methanesulfonyloxy-phenyl)purine. Melting point: 288°-291° C.

EXAMPLE 13

8-(2-Methoxy-4-methanesulfonyloxy-phenyl)-1H,3H-purin-2,6-dione

This compound was prepared analogous to Example 3 in aqueous sodium hydroxide, with the pH being maintained at between 10 and 10.5. Melting point 305°-307° C. (decomp.).

The following compounds were prepared analogously:

1,3-dimethyl-8-(2-methoxy-4-methanesulfonyloxy-phenyl)-1H,3H-purin-2,6-dione, Melting point: 239°-241° C.

1,3-dimethyl-8-(2-dimethylamino-4-methanesulfonylamino-phenyl)-1H,3H-purin-2,6-dione, 8-(2-dimethylamino-4-methanesulfonylamino-phenyl)-1H,3H-purin-2,6-dione.

EXAMPLE 14

8-(2-Methoxy-4-hydroxy-phenyl)-purin-2-one 3.5 g of 2-benzyloxy-8-(2-methoxy-4-benzyloxyphenyl)-purine (prepared by method A) was hydrogenated in 100 ml of ethanol in the presence of 1 g of 20% palladium-on-charcoal at 50° C. under a pressure of 5 bar. After the catalyst had been filtered off, the filtrate was concentrated by evaporation, the residue was extracted with 2N sodium hydroxide, and the product was precipitated by acidifying with glacial acetic acid. Further purification was effected by triturating with acetone. Yield: 0.22 g (10.6% of theory). Melting point: 250° C. (decomp.).

The following point was obtained analogously:
1,3-dimethyl-8-(2-methoxy-4-hydroxy-phenyl)-1H,3H-purin-2,6-dione (hydrogenation in the presence equivalents of potassium hydroxide). Melting point: above 310° C.

Calculated: C-56.00%; H-4.66%; N-18.50%. Found: C-55.63%; H-4.67%; N-18.53%. The compounds of the present invention, that is, those embraced by formula I above, tautomers thereof, and non-toxic, pharmacologically acceptable acid addition salts thereof, have useful pharmacodynamic properties. More particularly, they exhibit long-lasting hypotensive and/or positive inotropic activities in warm-blooded animals such as rats.

The pharmacodynamic properties of the compounds of the present invention were ascertained by the following method:

Determination of the effect on blood pressure and the positive inotropic effect in anesthetized cats The tests were carried out on cats which had been anesthetized with sodium pentobarbital (40 mg/kg i.p.). The animals breathed spontaneously. The arterial blood pressure was measured in the aorta abdominalis, using a Statham pressure transducer (P 23 Dc). To determine the positive inotropic effect, the pressure in the left ventricle was measured with a catheter-tip manometer (Millar PC-350 A). From this, the contractility parameter $dp/dt_{max}$ was obtained, using an analogue differentiator. The test compounds were injected into a vena femoralis. The solvent used was physiological saline solution of Polydiol 200. Each compound was tested on at least 3 cats, dosage 2 mg/kg i.v.

The following table shows the results obtained for a few representative species of the genus of formula I, where A=8-(2-methoxy-4-methanesulfonyloxy-phenyl)-3(1)H-purin-2-one,
B=2-(2-methoxy-4-methanesulfonyloxy-phenyl)-5-methanesulfonyloxy-imidazo[4,5-b]pyridine,
C=2-(2-methoxy-4-methanesulfonyloxy-phenyl)-4H-imidazo[4,5-b]pyridin-5-one,
D=2-(2-methoxy-4-methanesulfonyloxy-phenyl)-5H-imidazo[4,5-c]pyridin-4-one hydrochloride,
E=2-(2-methoxy-4-methanesulfonyloxy-phenyl)-4-methanesulfonyloxy-imidazo[4,5-c]pyridine,
F=2-(2-methoxy-4-propargyloxy-phenyl)=5H-imidazo[4,5-c]pyridin-4-one, and
G=2-(2-methoxy-4-methanesulfonyloxy-phenyl)-4H-imidazo[4,5-b]pyrazin-5-one.

| Compound | Increase in $dp/dt_{max}$ in % | Reduction in Blood Pressure in mm Hg | Duration of effective action (Half life) in minutes |
|---|---|---|---|
| A | +48 | −8/−6 | 42 |
| B | +53 | −50/−42 | 37 |
| C | +158 | −54/−54 | 31 |
| D | +117 | −42/−42 | 31 |
| E | +87 | −35/−27 | 29 |
| F | +138 | −59/−47 | 8 |
| G | +100 | −26/−27 | 5 |

The new compounds are well tolerated; thus, in the test on compounds A to G, no toxic effects on the heart or circulatory damage of any kind was observed.

In view of their pharmacological properties, the compounds of the present invention are useful for the treatment of cardiac insufficiency of various origins since they increase the contractile force of the heart and, by additionally lowering blood pressure, they facilitate the emptying of the heart.

For pharmaceutical purposes the compounds of the present invention are administered to warm-blooded animals perorally, parenterally or rectally as active ingredients in customary pharmaceutical compositions, that is, compositions consisting essentially of an inert pharmaceutical carrier and an effective amount of the active ingredient, such as tablets, coated pills, capsules, wafers, powders, solutions, suspensions, emulsions, syrups, suppositories and the like. An effective amount of the compounds of the present invention is from 0.1 to 5 mgm/kg body weight, preferably 0.5 to 2.0 mgm/kg body weight, 1 to 4 times daily.

The following examples illustrate a few pharmaceutical compositions comprising a compound of the present invention as an active ingredient and represent the best modes contemplated of using the invention. The parts are parts by weight unless otherwise specified.

EXAMPLE 15

Tablets

The tablet composition is compounded from the following ingredients:

| | |
|---|---|
| 2-(2-Methoxy-4-methanesulfonyloxy-phenyl)-5H—imidazo[4,5-c]pyridin-4-one hydrochloride | 100.0 parts |
| Lactose | 50.0 parts |
| Polyvinylpyrrolidone | 5.0 parts |
| Carboxymethylcellulose | 19.0 parts |
| Magnesium stearate | 1.0 parts |
| | 175.0 |

Preparation:

Moist screening: 1.5 mm Drying: Circulating air dryer, 50° C Dry screening: 1 mm Add the remaining excipients to the granulate and compress the final mixture into 175 mg-tablets. Each tablet contains 100 mg of the active ingredient.

Example 16

Coated tablets

The tablet core composition is compounded from the following ingredients:

| | |
|---|---|
| 2-(2-methoxy-4-methanesulfonyloxy-phenyl)-5H—imidazo[4,5-c]pyridin-4-one hydrochloride | 50.0 parts |
| Dried corn starch | 20.0 parts |
| Soluble starch | 2.0 parts |
| Carboxymethylcellulose | 7.0 parts |
| Magnesium stearate | 1.0 parts |
| | 80.0 parts |

Preparation:

Moisten the active ingredient and starch evenly with an aqueous solution of the soluble starch.

Moist screening: 1.0 mm Dry screening: 1.0 mm Drying: 50° C. in a circulating air dryer.

Mix the granulate and remaining excipients and compress into 80 mg-tablet cores.

The finished cores are provided with a sugar coating in the usual way in a coating vessel. Weight of coated tablet: 120 mg, each containing 50 mg of the active ingredient.

EXAMPLE 17

Suppositories

The suppository composition is compounded from the following ingredients:

| | |
|---|---|
| 2-(2-Methoxy-4-methanesulfonyloxy-phenyl)-5H—imidazo[4,5-c]pyridin-4-one-hydrochloride | 75.0 parts |
| Suppository base (e.g. cocoa butter) | 1625.0 parts |
| | 1700.0 parts |

Method of preparation:

The suppository base is melted. At 38° C. the ground active ingredient is homogeneously dispersed in the melt. It is cooled to 35° C. and poured into chilled suppository molds. Weight of suppository: 1.7 g containing 75 mg of the active ingredient.

EXAMPLE 18

Hypodermic solution

The solution is compounded from the following ingredients:

| | |
|---|---|
| 2-(2-Methoxy-4-methanesulfonyloxy-phenyl)-5H—imidazo[4,5-c]pyridin-4-one hydrochloride | 50.0 parts |
| Sorbitol | 250.0 parts |
| Distilled water q.s.ad | 5000.0 parts by vol. |

Preparation:

The active ingredient and sorbitol are dissolved in distilled water, the solution is diluted to the stated volume and filtered under sterile conditions.

Packaging: in 5 ml ampules, each containing 50 mg of the active ingredient.

Sterilizing: 20 minutes at 120° C.

EXAMPLE 19

Drop solution

The solution is compounded from the following ingredients:

| | |
|---|---|
| 2-(2-Methoxy-4-methanesulfonyloxy-phenyl)-5H—imidazo[4,5-c]pyridin-4-one hydrochloride | 5.0 parts |
| Methyl p-hydroxybenzoate | 0.035 parts |
| Propyl p-hydroxybenzoate | 0.015 parts |
| Anisole | 0.05 parts |
| Menthol | 0.06 parts |
| Sodium saccharin | 1.0 parts |
| Glycerol | 10.0 parts |
| Ethanol | 40.0 parts |
| Distilled water q.s.ad | 100.0 parts by vol. |

Preparation:

The benzoates are dissolved in ethanol, and then the anisole and menthol are added. The active ingredient, glycerol and sodium saccharin dissolved in water are then added. The solution is then filtered until clear.

Any one of the other compounds embraced by formula I, a tautomer thereof or a non-toxic, pharmacologically acceptable acid addition salt thereof may be substituted for the particular active ingredient in Examples 15 through 19. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

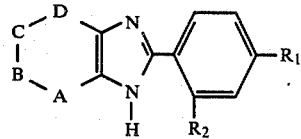

wherein,
among the four ring members A, B, C or D, one is —N=, two are —CH=, and one is

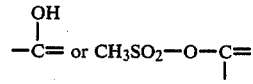

$R_1$ is NC—CH$_2$—O—, HOOC—CH$_2$—O—, $R_3$—OOC—CH$_2$—O—, $R_3SO_2$—O—, $R_3SO_2$—NH—, $R_3SO_2$—NR$_3$— or $R_4$—O—;
$R_2$ is $R_3$O—,

$R_5$—O—;
$R_3$ is alkyl of 1 or 4 carbon atoms;
$R_4$ is alkynyl of 2 of 5 carbon atoms; and
$R_5$ is alkenyl of 2 of 5 carbon atoms or alkynyl of 2 to 5 carbon atoms;
a tautomer thereof; or a non-toxic, pharmacologically acceptable acid addition salt thereof.

2. A compound of claim 1, where
A, B, C, D, $R_1$ and $R_2$ have the meanings defined in claim 1;
$R_3$ is methyl;
$R_4$ is propargyl; and
$R_5$ is allyl or propargyl;
a tautomer therof; or a non-toxic, pharmacologically acceptable acid addition salt thereof.

3. An imidazo[4,5-b]pyridin-5-one, imidazo[4,5-c]-pyridin-4-one or imidazo[4,5-c]pyridin-6-one of claim 1, where
$R_1$ is propargyloxy, methanesulfonyloxy, methanesulfonylamino or N-methyl-methanesulfonylamino; and $R_2$ is methoxy or dimethylamino;
a tautomer thereof; or a non-toxic, pharmacologically acceptable acid addition salt thereof.

4. A compound of claim 3, where
$R_2$ has the meanings defined in claim 1; and
$R_1$ is methanesulfonyloxy, methanesulfonylamino or N-methyl-methanesulfonylamino;
a tautomer thereof; or a non-toxic, pharmacologically acceptable acid addition salt thereof.

5. A compound of claim 1, which is 2-(2-methoxy-4-methanesulfonyloxy-phenyl)-5H-imidazo[4,5-c]pyridin-4-one, a tautomer thereof; or a non-toxic, pharmacologically acceptable acid addition salt thereof.

6. A compound of claim 1, which is 2-(2-methoxy-4-methanesulfonyloxy-phenyl)-5-methanesulfonyloxy-imidazo[4,5-b]pyridine, a tautomer thereof; or a non-toxic, pharmacologically acceptable acid addition salt thereof.

7. A compound of claim 1, which is 2-(2-methoxy-4-methanesulfonyloxy-phenyl)-4H-imidazo[4,5-b]pyridin-5-one, a tautomer thereof; or a non-toxic, pharmacologically acceptable acid addition salt thereof.

8. A compound of claim 1, which is 2-(2-methoxy-4-methanesulfonyloxy-phenyl)-4-methanesulfonyloxy-imidazo[4,5-c]pyridine, a tautomer thereof; or a non-toxic, pharmacologically acceptable acid addition salt thereof.

9. A compound of claim 1, which is 2-(2-methoxy-4-propargyloxy-phenyl)-5H-imidazo[4,5-c]pyridin-4-one, a tautomer thereof; or a non-toxic, pharmacologically acceptable acid addition salt thereof.

10. A hypotensive or cardiotonic pharmaceutical composition consisting essentially of an inert pharmaceutical carrier and an effective hypotensive or cardiotonic amount of a compound of claim 1.

11. The method of lowering the blood pressure or increasing the contractility of the heart muscle in a warm-blooded animal in need thereof, which comprises perorally, parenterally or rectally administering to said animal an effective hypotensive or positive inotropic amount of a compound of claim 1.

* * * * *